United States Patent [19]
Blake, III

[11] Patent Number: 5,281,220
[45] Date of Patent: Jan. 25, 1994

[54] ENDOSCOPIC INSTRUMENT

[76] Inventor: Joseph W. Blake, III, 9 Taylor Ave., Norwalk, Conn. 06854

[21] Appl. No.: 819,771

[22] Filed: Jan. 13, 1992

[51] Int. Cl.⁵ .................. A61B 17/28; A61B 17/32
[52] U.S. Cl. .................................. 606/46; 606/47; 606/51; 606/52; 606/113; 606/148; 606/170; 606/174; 606/205
[58] Field of Search ............................. 606/205–208, 606/170, 171, 174, 47, 52, 51, 142, 148, 113, 46; 128/751

[56] References Cited

U.S. PATENT DOCUMENTS

| | | | |
|---|---|---|---|
| 4,258,716 | 3/1981 | Sutherland | 606/174 X |
| 4,848,338 | 7/1989 | De Satnick et al. | 606/171 X |
| 5,147,373 | 9/1992 | Ferzli | 606/207 X |

Primary Examiner—Michael H. Thaler
Attorney, Agent, or Firm—Patrick J. Walsh

[57] ABSTRACT

An improved endoscopic instrument suitable for performing internal procedures through a trocar in which the instrument handle is provided with a control mechanism for rotating the instrument thereby enabling a surgeon to manipulate and utilize the instrument with one hand.

7 Claims, 2 Drawing Sheets

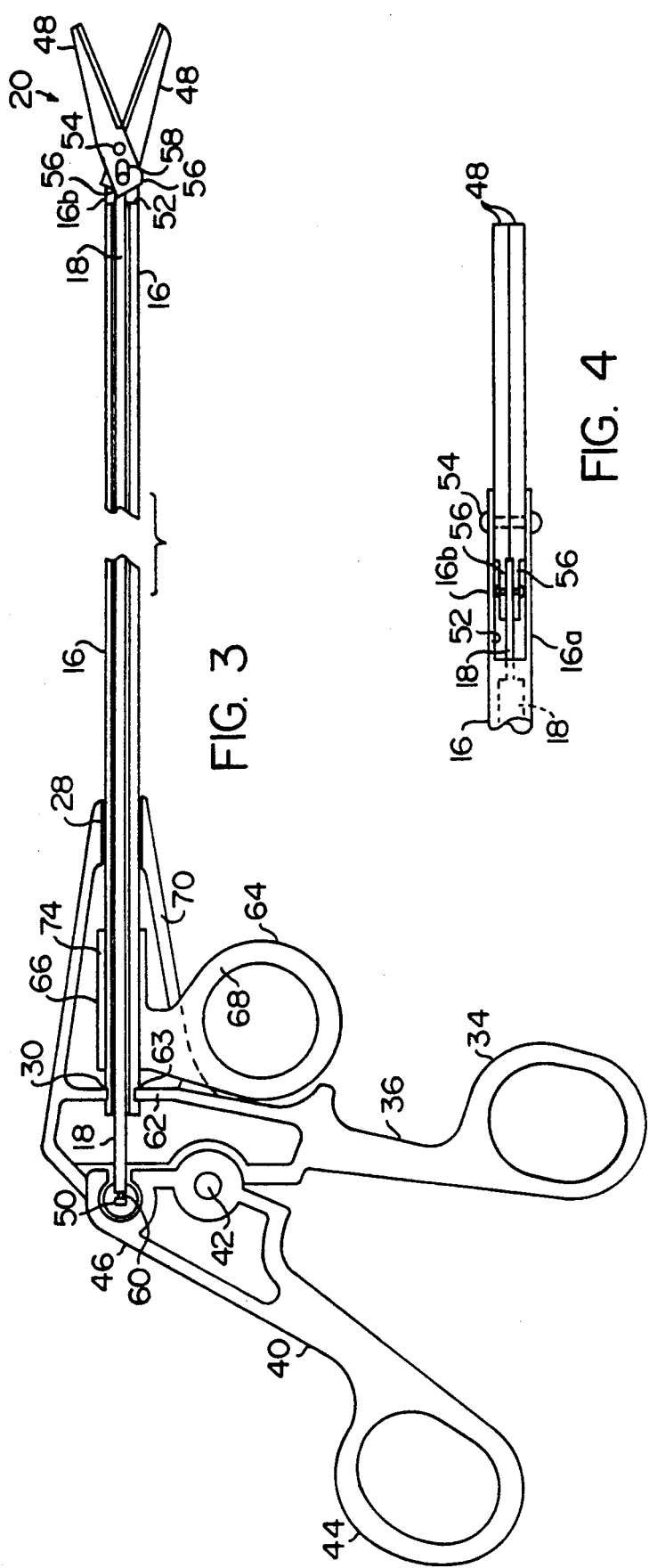

ENDOSCOPIC INSTRUMENT

BACKGROUND OF THE INVENTION

The present invention relates to medical instruments particularly endoscopic instruments used for procedures such as internal surgery.

Conventional endoscopic instruments for internal surgery such as scissors, graspers, ligators, forceps, dissectors, endoloops, cautery, etc., are useable with a surgical trocar. The instruments comprise an operating handle, an elongate tube for projecting the instrument through a trocar, and working components such as scissor blades fitted to the operating end of the elongate tube. The tube encases a linkage interconnecting the handle and the working components so that by manipulating the handles the instrument is employed. In operation it is usually necessary to rotate the working components with respect to the longitudinal axis of the elongate tube in order to place the instrument in proper orientation for a medical procedure. Conventional instruments include a rotary wheel attached to the elongate tube for rotating the tube and working components as necessary to achieve proper orientation. This arrangement is simple and straightforward, however the arrangement does require the operator to use both hands, i.e., the right hand manipulates the instrument handle while the left manipulates the rotary wheel to orient the instrument working components to correct angle of attack. There is need for an endoscopic instrument enabling a surgeon to use only one hand for orienting and actuating the working components of the instrument.

SUMMARY OF THE INVENTION

The present invention is directed to an improved endoscopic instrument and comprises a new and useful handle arrangement for enabling a surgeon to use only one hand for orienting instrument working components into proper angle of attack and for actuating them as required for a medical procedure. According to one embodiment of the invention, an improved surgical instrument includes working components such as scissor blades fitted to a reciprocating handle by which the blades are actuated. The handle manipulates the blades by means of a linkage extending through an elongate tube. The linkage transmits reciprocating handle motion to the scissor blades to accomplish the desired function. The linkage, the tube, and the scissor blades rotate as a unit about the longitudinal tube axis with respect to the handle. According to the invention, the operating handle includes a slide member enabling the surgeon to rotate the scissor blades with the same hand used for actuating the blades. The slide member forms part of the handle assembly and includes a cylinder having a spiral cam groove fitted over the elongate tube. The elongate tube includes a cam follower riding in the spiral groove so that longitudinal movement of the slide member induces rotary movement of the elongate tube and scissor blades. The slide member includes a control loop for manipulation by the surgeon.

As a result, the invention enables a surgeon to grasp and employ an endoscopic instrument such as surgical scissors in one hand.

OBJECTS OF THE INVENTION

An object of the invention to provide an improved endoscopic instrument for one hand operation.

A further object of the invention to provide a surgical instrument having a handle arrangement enabling a surgeon to use one hand for orienting and actuating the instrument.

It is a further object of the invention to provide a reliable easy to use mechanism for rotation of the working components of a surgical instrument.

Another object of the invention is to provide an improved mechanism for orienting and actuating a variety of endoscopic instruments including scissors, forceps, ligators, graspers, dissectors, cautery, endoloops and the like.

Other and further objects of the invention will occur to one skilled in the art with an understanding of the following detailed description of the invention or upon employment of the invention in practice.

DESCRIPTION OF THE DRAWING

A preferred embodiment of the invention has been chosen for purposes of illustrating the construction and operation of the improved endoscopic instrument and is shown in the accompanying drawing in which:

FIG. 3 is a section view of the instrument of FIG. 1 showing its interior linkage for manipulating the instrument.

FIG. 4 is an enlarged fragmentary plan view of the far end of the instrument showing arrangement of operating components.

DETAILED DESCRIPTION OF THE INVENTION

Figure 1:
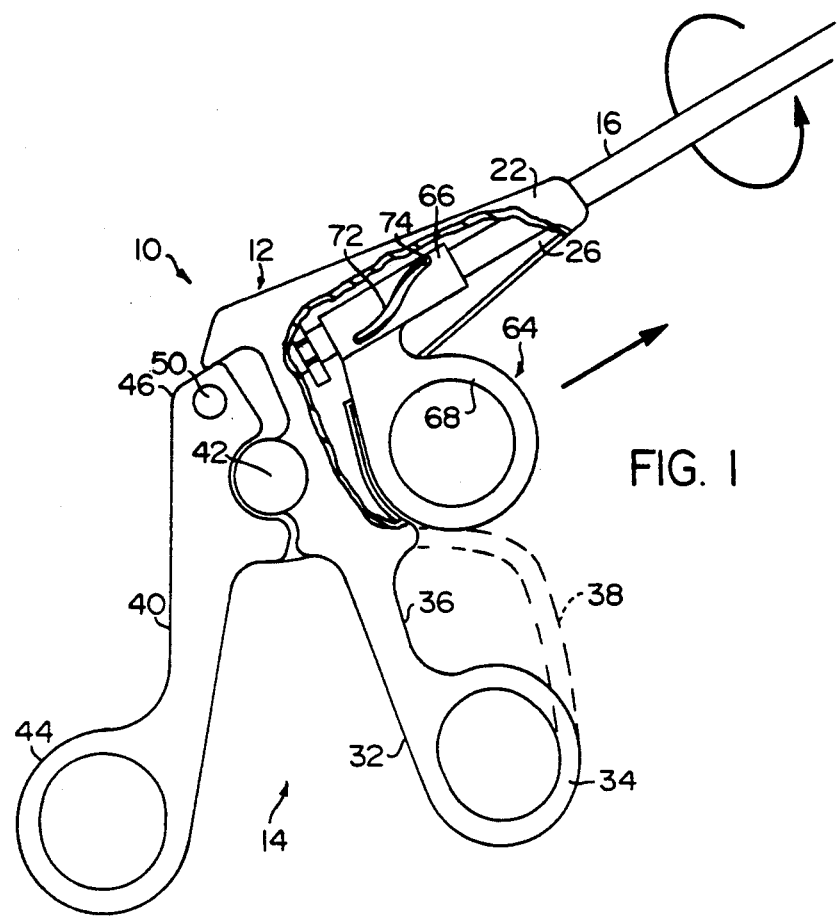
FIG. 1 is a right side elevation view of an instrument according to the invention with the instrument frame partially broken away to illustrate interior components.
Figure 2:
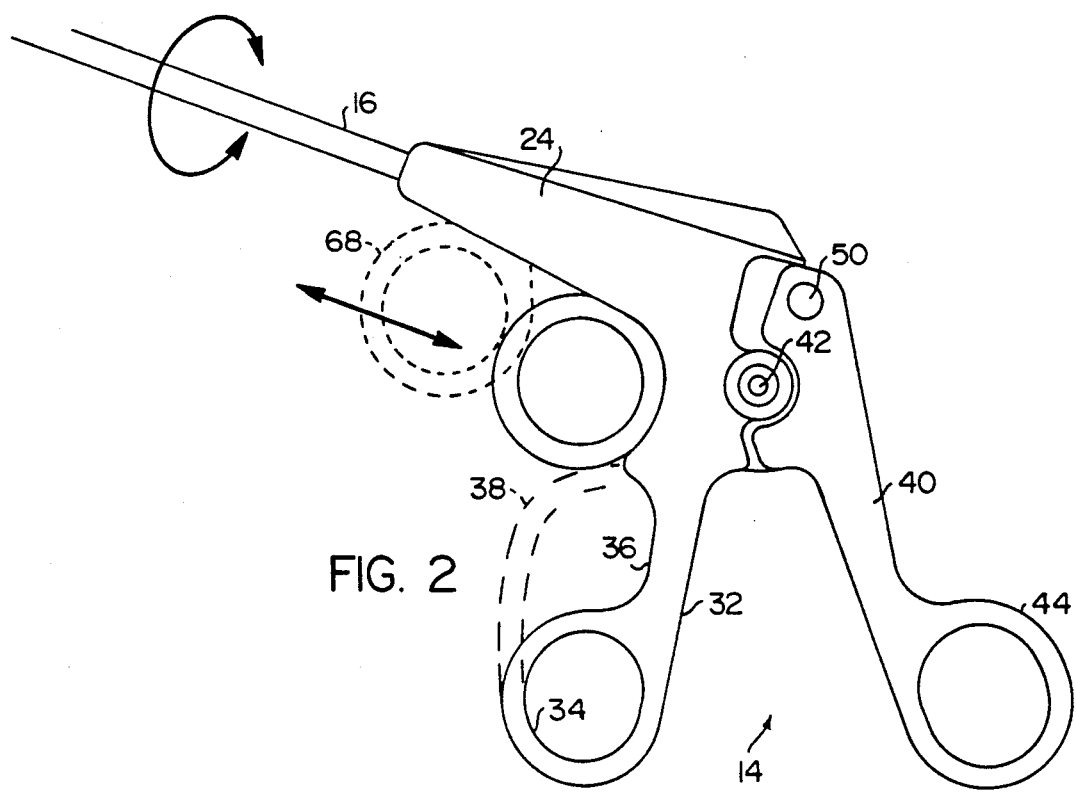
FIG. 2 is a left side elevation view of the instrument of FIG. 1 showing the control loop in advanced position.

Referring now to the drawing, an endoscopic instrument 10 according to the invention comprises an instrument housing or frame 12, a handle assembly 14, an elongated tube 16 projecting from the instrument housing and encasing an actuating linkage 18 (FIG. 3), and operating components 20 projecting from the far end of the tube for use in surgery or other endoscopic or laparoscopic procedure.

The instrument housing comprises right 22 and left 24 plates molded of a suitable plastic. The plates are joined at their peripheries and define an upper chamber 26 and the depending handle assembly 14. The upper chamber has spaced, aligned openings 28, 30 (FIG. 3) for receiving and rotatably supporting the elongated linkage tube 16, and for projecting the tube at approximately a right angle from the housing. The handle assembly 14 includes a stationary hand grip 32 depending from the housing and terminating in a finger loop 34 which in normal use receives at least one finger, usually the ring finger. A recess or notch 36 in the hand grip above the loop accommodates the middle finger. Alternatively, the loop 38 may be enlarged as shown in dash lines to receive several fingers.

The handle assembly further comprises a moveable hand lever 40 pivotally attached to the housing at pivot axis 42 and having at its lower end a finger loop 44 for receiving a surgeon's thumb. At its upper end 46 the hand lever is attached to the linkage 18 which manipulates the operating components, as for example, scissor blades. A squeeze of the handle produces a pull on the linkage thereby closing the blades. The blades are opened by opening the handle. If desired, the positions of the hand lever 40 and the hand grip 32 may be reversed such that the forward handle member 32 is pivoted to the stationary instrument housing and the rear handle member 40 is affixed to the housing.

The blade actuating linkage is shown in FIGS. 3 and 4, and comprises the elongate tube 16 encasing a link or rod 18 extending through the tube and interconnecting scissor blades 48 and a thrust bearing 50. The blades project from a longitudinal slot 52 at the far end of the tube and are pivoted together in scissor fashion by means of a pivot pin 54 extending through end portions 16 a-b of the tube wall. The tube wall portions 16 a-b define the slot 52 and extend above and below the blades. Blade tangs 56 extend beyond the pivot axis 54 a short distance into the tube and are there connected to an end of the link 18. Each tang is slotted 58 (FIG. 3) for sliding connection of the link so that a push on the link (opening the handle) opens the blades while a pull on the link (squeeze of the handle) closes them.

The link at its other end is connected to thrust bearing 50 which applies push and pull thrusts to the link. The thrust bearing is encased in the hand lever 40 so that by opening and closing the scissor handle corresponding push and pull forces are applied to the blade link.

As shown in FIG. 3, the elongated tube subassembly is free to rotate about its long axis with respect to the stationary frame by means of a slip collar coupling 60 between link 18 and thrust bearing 50, by cylindrical bore or opening 28 receiving the tube through the front end of the housing, and by means of housing collar 62 engaging tube recess 63 at aligned opening 30. The collar 62 and recess 63 retain the tube in fixed longitudinal position while link 18 is capable of limited longitudinal movement in the tube to accommodate the push-/pull motion required for opening and closing the blades.

In accordance with the invention, the stationary frame is fitted with a slide member 64 for rotating the tube, link and blade subassembly. The slide member includes a cylinder or barrel cam 66 fitted over the tube within the housing chamber and being capable of relatively free longitudinal sliding movement along the tube 16. The cylinder is connected to a depending finger loop 68 for engagement by an index finger. The finger loop projects through a narrow slit 70 in the frame for limiting the slide member and cylinder to longitudinal movement along the frame and tube. A spiral cam groove 72 is cut through the cylinder wall and extends circumferentially of the cylinder. A cam follower 74 is affixed to the tube and projects radially of the tube into the cam groove. It will be understood that by moving the cylinder along the tube in the direction of the arrow (FIG. 1), the tube will rotate with the degree of rotation determined directly by distance of cylinder movement and groove pitch or contour. Preferably, the excursion of the slide member within the confines of the frame slot 70 produces a full rotation, i.e. 360 deg., of the tube and scissor blade subassembly and the spiral groove is positioned on the cylinder to accomplish this result. In practice, other groove contours of less than 360 deg. may be used according to the normal operating requirements of particular instruments. It is desirable that the slide member move smoothly with application of finger force and hold the position or orientation selected for the scissor blades.

In this description, endoscopic scissors are presented as an illustrative embodiment with the understanding that the invention applies to each of the instruments listed above as well as other instruments as may now or hereafter be used for endoscopic or laparoscopic procedures.

I claim:

1. An endoscopic instrument comprising a handle assembly having a fixed grip and a movable grip pivoted to the fixed grip, an elongate tube having one end fitted to the handle assembly for rotation of the tube about its longitudinal axis and another end mounting instrument working components, a linkage extending through the tube and interconnecting the components with the handle assembly so the components are actuated by manipulation of the movable grip by one hand, control means slidably mounted on the handle assembly for rotating the tube, the control means having a cylindrical portion fitted to and coaxial with the tube and having a depending integral finger loop available for manipulation by the index finger of the one hand, and means interconnecting the cylinder and tube so that a linear movement of the cylinder induces rotary movement of the tube and components.

2. An instrument as defined in claim 1 in which the means interconnecting the cylinder and tube comprises a spiral cam groove on the cylinder and a cam follower on the tube positioned in the cam groove.

3. An instrument as defined in claim 2 in which the spiral cam groove accommodates up to 360 deg. rotation of the instrument components.

4. An instrument as defined in claim 1 in which the working components are one on the following: scissors, cautery, forceps, graspers, dissectors, ligator, or an endoloop.

5. An endoscopic instrument comprising a housing formed of confronting plates joined at their peripheries and defining an upper chamber and a depending handle assembly having a fixed grip and a movable lever,
    an elongate tube having one end fitted to the housing and another end deploying operating components, a linkage extending through the tube and interconnecting the components with the handle assembly so the components are actuated by manipulation of the movable lever,
    the tube, linkage and operating components being mounted on the housing for rotation as a unit about the long axis of the tube;
    means forming part of the handle assembly for rotating the tube about said axis utilizing the same hand employed for actuation of the operating components,
    and the means for rotating including a slidable member having a finger loop positioned adjacent the fixed grip and having a barrel cam fitted onto the tube within the upper chamber, a spiral groove extending circumferentially of the cam, a cam follower on the tube engaging the groove so that movement of the finger loop by the same hand employed for actuation of the operating components causes rotation of the components about the long axis.

6. An instrument as defined in claim 5 in which the spiral cam groove accommodates up to 360 deg. rotation of the operating components.

7. An instrument as defined in claim 5 in which the operating components are one of the following: scissors, cautery, forceps, graspers, dissectors, ligator, or an endoloop.

* * * * *